US00PP20683P2

(12) United States Plant Patent
Darques

(10) Patent No.: US PP20,683 P2
(45) Date of Patent: Jan. 26, 2010

(54) ***HEUCHERA* PLANT NAMED 'DARK SECRET'**

(50) Latin Name: ***Heuchera* hybrid**
Varietal Denomination: Dark Secret

(76) Inventor: Gerard Darques, 66 Rue des Tronchants, Lorgies (FR)

( * ) Notice: Subject to any disclaimer, the term of this patent is extended or adjusted under 35 U.S.C. 154(b) by 0 days.

(21) Appl. No.: 12/291,657

(22) Filed: Nov. 12, 2008

(51) Int. Cl.
*A01H 5/00* (2006.01)

(52) U.S. Cl. ..... Plt./440
(58) Field of Classification Search ..... Plt./440
See application file for complete search history.

*Primary Examiner*—Annette H Para
(74) *Attorney, Agent, or Firm*—Penny J. Aguirre

(57) ABSTRACT

A new cultivar of *Heuchera*, 'Dark Secret', characterized by its foliage that is dark purple-bronze in color with a silvery sheen with margins that are serrated and heavily ruffled, its petioles that are deep purple in color, its panicles of creamy white flowers held on purple stems, its vigorous growth habit, and its hardiness at least in U.S.D.A. Zones 4 to 9.

2 Drawing Sheets

Botanical classification: *Heuchera* hybrid.
Cultivar designation: 'Dark Secret'.

BACKGROUND OF THE INVENTION

The present invention relates to a new and distinct cultivar of *Heuchera* of hybrid origin and is hereinafter referred to by the cultivar name 'Dark Secret'.

The inventor discovered the new cultivar, 'Dark Secret', as a naturally whole plant mutation in his garden in Lorgies, France in spring of 2007. The parent plants of 'Dark Secret' are unknown, however *Heuchera* 'Frosted Violet' (U.S. Plant Pat. No. 15,085), *Heuchera* Crimson Curls (U.S. Plant Pat. No. 13,729) and *Heuchera* 'Obsidian' (U.S. Plant Pat. No. 14,836) are possible parents based on the characteristics of 'Dark Secret' and their proximity in the same growing area.

Asexual reproduction of the new cultivar was first accomplished under direction of the inventor by in vitro propagation in Rijswijk, The Netherlands in August of 2007. Asexual reproduction of the new cultivar has shown that the unique features of 'Dark Secret' are stable and reproduced true to type in successive generations.

SUMMARY OF THE INVENTION

The following traits have been repeatedly observed and represent the characteristics of the new cultivar. These attributes in combination distinguish 'Dark Secret' as a new and unique cultivar of *Heuchera*.

1. 'Dark Secret' exhibits foliage that is dark purple-bronze in color with a silvery sheen.
2. 'Dark Secret' exhibits foliage with margins that are serrated and heavily ruffled.
3. 'Dark Secret' exhibits petioles that are purple in color.
4. 'Dark Secret' exhibits panicles of creamy-white flowers on stems that are deep purple in color.
5. 'Dark Secret' exhibits a vigorous growth habit.

'Dark Secret' can be most closely compared to the cultivars that also the most probable parents. 'Obsidian' is similar to 'Dark Secret' in foliage coloration, however 'Obsidian' differs in having leaf margins that lack the serrations and ruffling of 'Dark Secret'. 'Frosted Violet' is similar to 'Dark Secret' in having foliage with a silver sheen to the surface, however 'Frosted Violet' differs from 'Dark Secret' in having foliage that is violet in color and lacks the margin ruffling that is observed with 'Dark Secret'. 'Crimson Curls' is similar to 'Dark Secret' in having heavily ruffled margins, however the foliage of 'Crimson Curls' is not as dark in color and the growth habit is not as vigorous as 'Dark Secret'.

BRIEF DESCRIPTION OF THE DRAWING

The accompanying colored photographs illustrate the overall appearance and distinct characteristics of the new *Heuchera*. The photographs were taken in The Netherlands of a plant one and a half years in age as grown outdoors in a 23-cm container.

The photograph in FIG. 1 provides a side view of new cultivar in bloom, the photograph in FIG. 2 is a close-up view of an inflorescence of 'Dark Secret', and the photograph in FIG. 3 provides a close-up view of a leaf and petiole of 'Dark Secret'.

Figure 1:
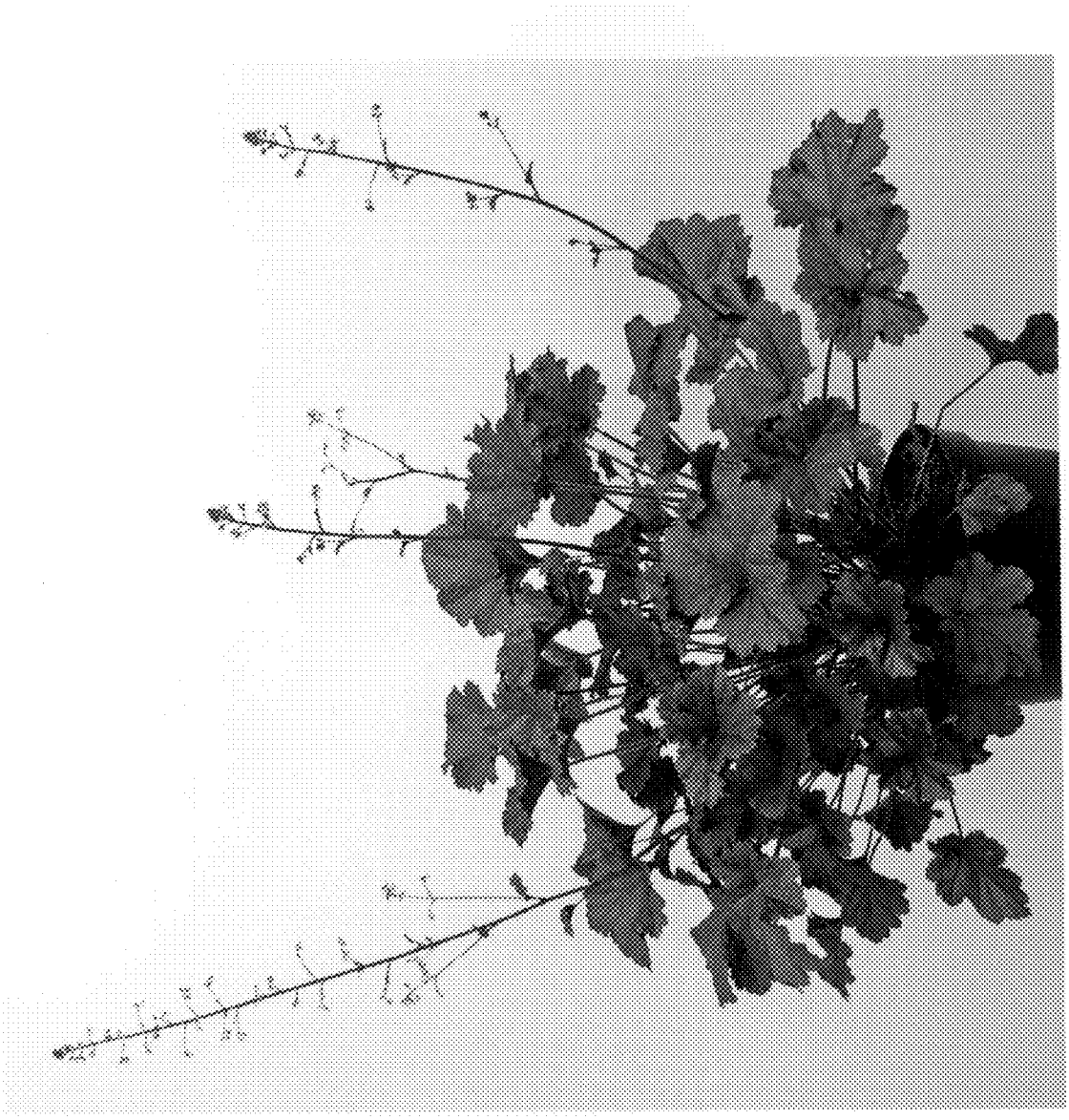
Figure 3:
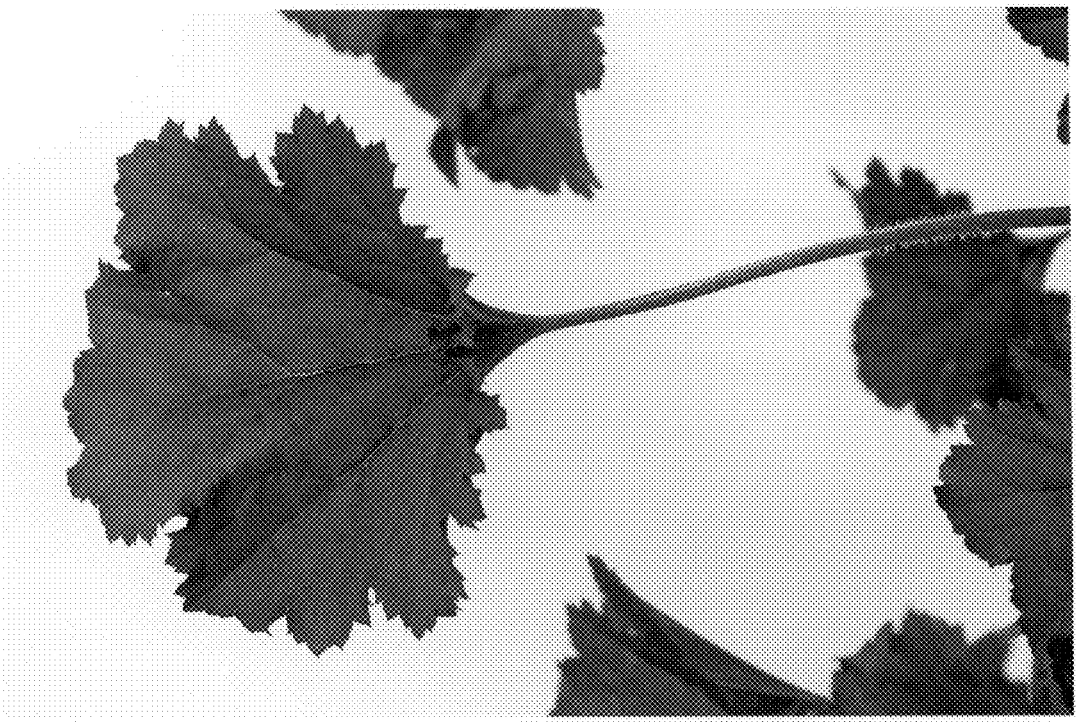
Figure 2:
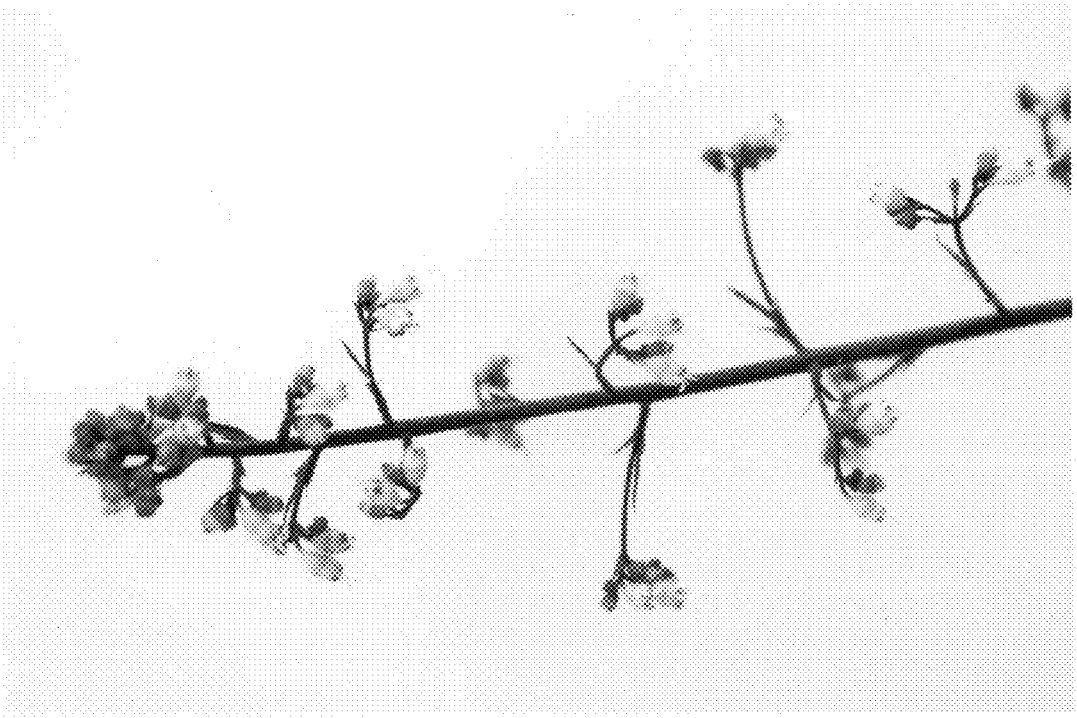

The colors in the photograph may differ slightly from the color values cited in the detailed botanical description, which accurately describe the colors of the new *Heuchera*.

DETAILED BOTANICAL DESCRIPTION OF THE PLANT

The following is a detailed description of a plant one and a half years in age as grown outdoors in a 23-cm container in The Netherlands. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Bloom period.*—Late spring to early summer.

*Plant habit.*—Compact, clump-forming herbaceous perennial, mounded foliage.

*Height and spread.*—Reaches about a height of about 36 cm in height (59 cm in height in bloom) and about 63 cm in width.

*Hardiness.*—At least in U.S.D.A. Zones 4 to 9.

*Diseases and pests.*—Disease free in the conditions tested, no susceptibility or resistance to pests has been observed.

*Root description.*—Fibrous roots on woody rootstalks.

*Branching habit.*—Basal rosettes of petiolate leaves emerging from short stems.

*Propagation.*—In vitro propagation is the preferred method, division are also possible.

*Growth rate.*—Vigorous in comparison to what is typically observed for *Heuchera* with dark colored foliage.

Stem description:

*Stem shape.*—Round, strong.

*Stem size.*—Average of 6.3 cm in length and 8 mm in width.

*Stem number.*—Average of 8 in a 23-cm container.

*Stem surface.*—Slightly glossy, moderately covered wih silky hairs about 3 mm in length and N155A in color.

*Internode length.*—Average of 6 mm.

*Stem color.*—59A to 187B to 187C.

Foliage description:

*Leaf shape.*—Orbicular.

*Leaf division.*—Simple.

*Leaf base.*—Hastate and moderately overlapping.

*Leaf apex.*—Acute.

*Leaf venation.*—Primary palmate, secondary net-veined, not conspicuous, vein color on upper and lower surface matches leaf color becoming 178A near base.

*Leaf margins.*—Lobed with an average of 7 per leaf, margins of lobes are serrated.

*Leaf attachment.*—Petiolate.

*Leaf arrangement.*—Rosette to alternate.

*Leaf orientation.*—Cupped inward and held mostly upright relative to petiole.

*Leaf surface.*—Upper surface is glabrous and dull, lower surface is rough to touch and pubescent with short hairs about 1 mm in length and about 186D in color.

*Leaf color.*—Young upper surface; N186A to N200A, young lower surface; N186C, mature leaves upper surface; N200A to 202A tinted with N186A to N189A, mature leaves lower surface; N77B.

*Leaf size.*—Average of 10.1 cm in length and 9.8 cm width.

*Leaf quantity.*—About 16 per stem.

*Petioles.*—Round in shape, an average of 20 cm in length and 3 mm in width, 178A in color with base tinged with 184A to 184B, surface is densely covered with hairs about 1.5 mm in length and 186D to N155B in color.

*Stipules.*—2 Leafy stipules at the base of each petiole, oblong in shape, an average of 1.7 cm in length and 2 mm in width, 185A to 187D in color (both surfaces), apex in narrowly acute, margins sparsely covered with short hairs.

Flower description:

*Inflorescence type.*—Numerous small bell-shaped flowers arranged on pyramidal panicles on flower scapes emerging from the base of the rosette, each peduncle has 2 pairs of lateral flowers and a terminal flower.

*Inflorescence size.*—An average of 59 cm in height and about 10.4 cm in width in full bloom.

*Inflorescence number.*—An average of 5 per 23-cm container.

*Flower fragrance.*—None detected.

*Flower quantity.*—Average of 200 flowers per flowering stem.

*Flower lastingness.*—Average of 4 days per flower, individual panicles blooms for about 3 weeks, flowers persistent.

*Flower buds.*—Broadly elliptic in shape, an average of 1.5 mm in diameter and 2.5 mm in depth, 59D in color with apex 182D.

*Flower aspect.*—Drooping to slightly outward on peduncles held nearly horizontal to rachis.

*Flower type.*—Campanulate.

*Flower size.*—About 2 mm in diameter and 5.5 mm in depth.

*Petals.*—About 5, rotate arrangement and implanted in hypanthium at base, narrowly elliptic in shape, margin is entire, apex is narrowly apiculate, upper and lower surface is glabrous and dull, color of upper and lower surface when opening and mature is N155B, about 2.5 mm in length and 0.5 mm in width.

*Calyx.*—Campanulate, sepals fused to hypanthium, 2.5 mm in depth and 2 mm in diameter.

*Sepals.*—5, un-fused portion is elliptic in shape, about 2.5 mm in length and 0.6 mm in width, margin is entire, apex is acute, base is fused, surface is densely covered with very short glandular hairs about 60A to 60B in color, color of upper surface is 59D with upper half 186D and tips 146A to 146B, color of upper and lower surface when immature is 59D with upper half 186D and tips 146A to 146B, color of upper and lower surface when mature is 145D with upper half 186D and tips 146A to 146B.

*Bracts.*—1, at base of peduncle, lanceolate in shape with 2 lateral and one terminal foliaceous appendages, N189A in color, about 8 mm in length and 2 mm in width, acute-leafy apex, base truncate and fused to peduncle.

*Peduncles.*—Average of 5.2 cm in length and an average of 0.8 mm in width, held nearly horizontal to rachis, color 187A.

*Pedicels.*—Average of 2 mm in length and 0.3 mm in width, color 187A, slightly puberulent surface, terminal is straight from peduncle and laterals are held at about a 45° angle.

*Rachis (flower scape).*—Average of 58 cm in length and an average of 3 mm in width, 187A in color, surface is slightly puberulent, peduncle internode length is an average of 2 cm.

Reproductive organs:

*Gynoecium.*—2 Pistils, club-shaped, about 4 mm in length, stigmas minute and N155B to N155C in color, styles are about 3.5 mm in length and N155B to N155C in color, ovaries are superior and 144C in color.

*Androcoecium.*—About 5 stamens, anthers are ovate in shape, basifixed, about 0.4 mm in diameter and 23B in color, filaments are about 1 mm in length and N155B to N155C in color, no pollen was observed.

*Seed.*—Seed development has not been observed.

It is claimed:

1. A new and distinct cultivar of *Heuchera* plant named 'Dark Secret' as herein illustrated and described.

* * * * *